(12) United States Patent
Oh

(10) Patent No.: US 11,160,521 B2
(45) Date of Patent: Nov. 2, 2021

(54) METHOD FOR 3D IMAGE RECONSTRUCTION

(71) Applicant: HDT CO., LTD., Gwangju (KR)

(72) Inventor: Joon Ho Oh, Gwangju (KR)

(73) Assignee: HDT CO., LTD., Gwangju (KR)

( * ) Notice: Subject to any disclaimer, the term of this patent is extended or adjusted under 35 U.S.C. 154(b) by 80 days.

(21) Appl. No.: 16/722,558

(22) Filed: Dec. 20, 2019

(65) Prior Publication Data

US 2021/0186445 A1    Jun. 24, 2021

(51) Int. Cl.
*A61B 6/00* (2006.01)

(52) U.S. Cl.
CPC ............ *A61B 6/466* (2013.01); *A61B 6/5223* (2013.01); *A61B 6/5229* (2013.01); *A61B 6/563* (2013.01)

(58) Field of Classification Search
None
See application file for complete search history.

(56) References Cited

U.S. PATENT DOCUMENTS

| 2003/0194049 A1* | 10/2003 | Claus ................... G06T 11/006 378/22 |
| 2020/0184639 A1* | 6/2020 | Park ......................... G06T 7/11 |
| 2021/0004994 A1* | 1/2021 | Kubo ...................... G06T 11/00 |

FOREIGN PATENT DOCUMENTS

| JP | 6505513 B2 | 4/2019 |
| KR | 10-2012-0097563 A | 9/2012 |
| KR | 10-2013-0081798 A | 7/2013 |
| KR | 10-2014-0087206 A | 7/2014 |

* cited by examiner

*Primary Examiner* — Hoon K Song
(74) *Attorney, Agent, or Firm* — The PL Law Group, PLLC

(57) ABSTRACT

A method for 3D image reconstruction includes the steps of radiating an X-ray source at a predetermined angle to a photographing subject and acquiring a plurality of two-dimensional image images received through a detector, generating an image population by scaling the obtained plurality of two-dimensional image images, generating a virtual image using a pixel average between two-dimensional images from the plurality of scale-corrected two-dimensional images, and adding the virtual image to the image population, repeatedly generating a virtual image using a pixel average between two-dimensional images included in the image population until a two-dimensional image larger than a predetermined number P is generated in the image population, and generating a 3D video image using the generated 2D video image.

4 Claims, 8 Drawing Sheets

METHOD FOR 3D IMAGE RECONSTRUCTION

TECHNICAL FIELD

The present invention relates to a method for 3D image reconstruction, and more particularly, to a method of reconstructing a 3D image using a small number of 2D images.

BACKGROUND ART

An X-ray inspection apparatus or a CT apparatus is an apparatus that obtains an internal image of a subject by using an x-ray source. The X-ray inspection apparatus or the CT apparatus radiates an X-ray source to a subject, detects an X-ray source passing through the subject, and images the inside of the subject in three dimensions. Accordingly, the X-ray inspection apparatus or the CT apparatus can identify the inside of a subject that cannot be seen from the outside, and thus is used in many parts such as medical and inspection.

However, conventional X-ray inspection apparatus emits hundreds or thousands of X-ray sources to image the inside of a subject in three dimensions. This has a problem in that a high exposure amount is exposed to the subject.

In this regard, an X-ray CT imaging apparatus (Korean Patent Publication No. 10-2012-0097563) and the like are disclosed which minimizes X-ray dose applied to a patient using a cone beam. However, there is a problem in that hundreds to thousands of two-dimensional images can be obtained while rotating a subject and a three-dimensional image can be generated using the same in order to generate a three-dimensional image.

Therefore, a research on a 3D image reconstruction method capable of imaging a 3D image using a small number of 2D images is required.

SUMMARY

The present invention provides a three-dimensional image reconstruction method which after obtaining a small number of 2D images, a virtual image is generated using the acquired images and used for generating 3D images, thereby minimizing the exposure of radiation through 2D imaging.

The present invention provides a three-dimensional image reconstruction method capable of realizing a three-dimensional image by minimizing image distortion by correcting an image scale between two-dimensional images taken from multiple angles and using the same to reconstruct the three-dimensional image.

Method for 3D Image Reconstruction

A method for 3D image reconstruction according to the present invention to achieve the above object, including the steps of radiating an X-ray source at a predetermined angle to a photographing subject and acquiring a plurality of two-dimensional image images received through a detector; generating an image population by scaling the obtained plurality of two-dimensional image images; generating a virtual image using a pixel average between two-dimensional images from the plurality of scale-corrected two-dimensional images, and adding the virtual image to the image population; repeatedly generating a virtual image using a pixel average between two-dimensional images included in the image population until a two-dimensional image larger than a predetermined number P is generated in the image population; and generating a 3D video image using the generated 2D video image.

According to one aspect of the invention, in the step of generating of the image population by the scale correction, the first side image and the second side image may be scale-corrected to the size of the vertical image.

According to another aspect of the invention, in the step of repeatedly generating the virtual image, a virtual image is generated over a plurality of times ($2n$ virtual images are generated at the time of nth generation), and the virtual image is repeatedly generated as many times as the number corresponding to n calculated by Equation 1 below.

$$P \leq \sum_{k=1}^{n} 2^k, \quad \text{[Equation 1]}$$

where P is a predetermined number.

According to an embodiment of the present invention, there is provided a three-dimensional image reconstruction method that can minimize radiation exposure through minimal two-dimensional imaging, after obtaining a small number of two-dimensional image, by using the obtained image to generate a virtual image and to use it to generate a three-dimensional image.

And according to an embodiment of the present invention, there is provided a three-dimensional image reconstruction method that by correcting an image scale between two-dimensional images taken from multiple angles and reconstructing the three-dimensional image, a three-dimensional image can be realized by minimizing image distortion.

DETAILED DESCRIPTION

Figure 1:
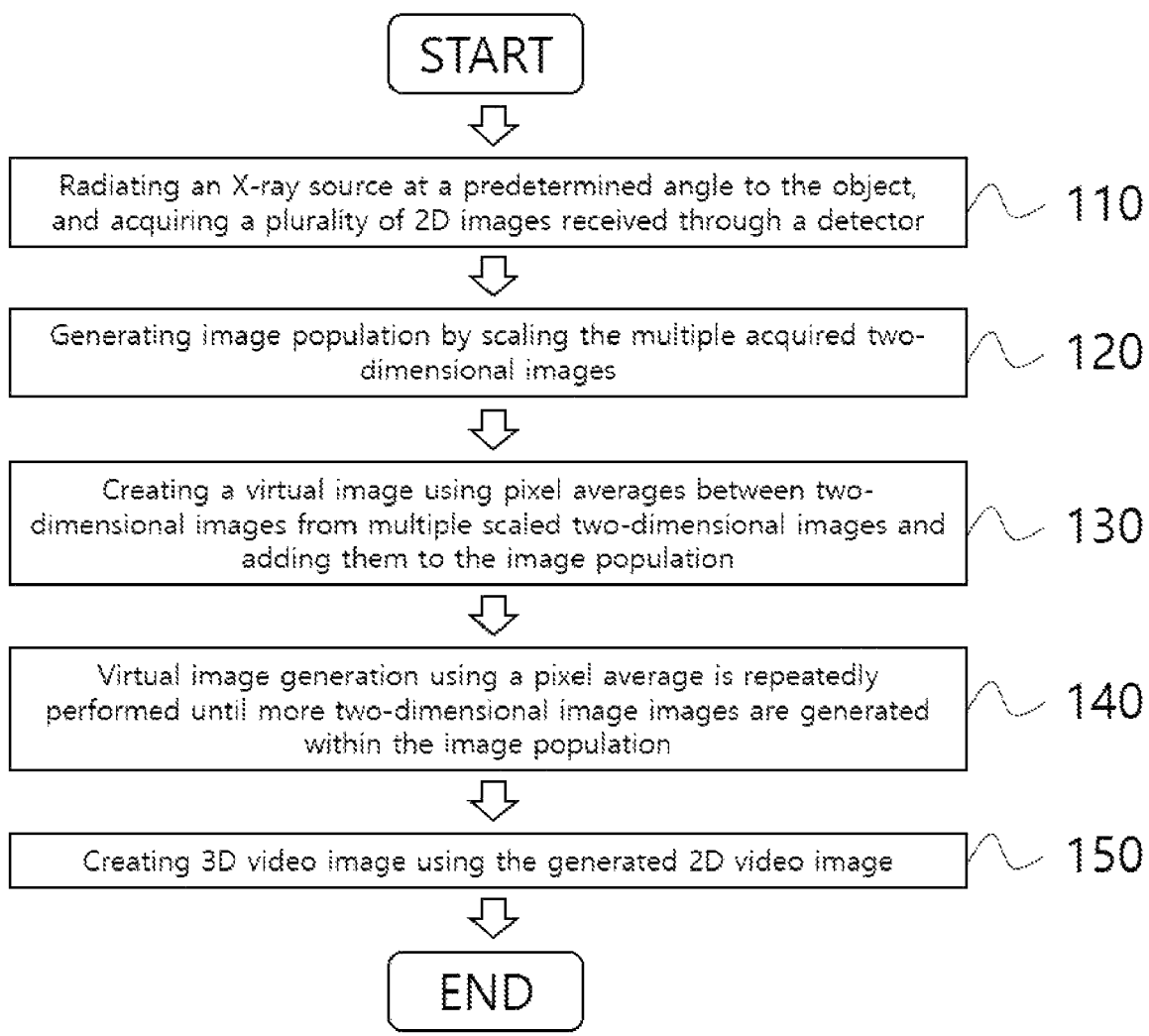
FIG. 1 is a flowchart illustrating a method for 3D image reconstruction according to an embodiment of the present invention.

Hereinafter, with reference to the accompanying drawings will be described in more detail a method for 3D image reconstruction according to an embodiment of the present invention. However, the present invention is not limited by the embodiments. Same reference numerals in the drawings denote same elements.

In an embodiment of the present invention, there is provided a method that in the process of inspecting the inside of a subject through an X-ray inspection apparatus, a two-dimensional image of various angles may be reconstructed into a three-dimensional image, and a three-dimensional image may be configured using a minimum number of two-dimensional images.

Hereinafter, the 3D image reconstruction method will be described in more detail.

Figure 2:
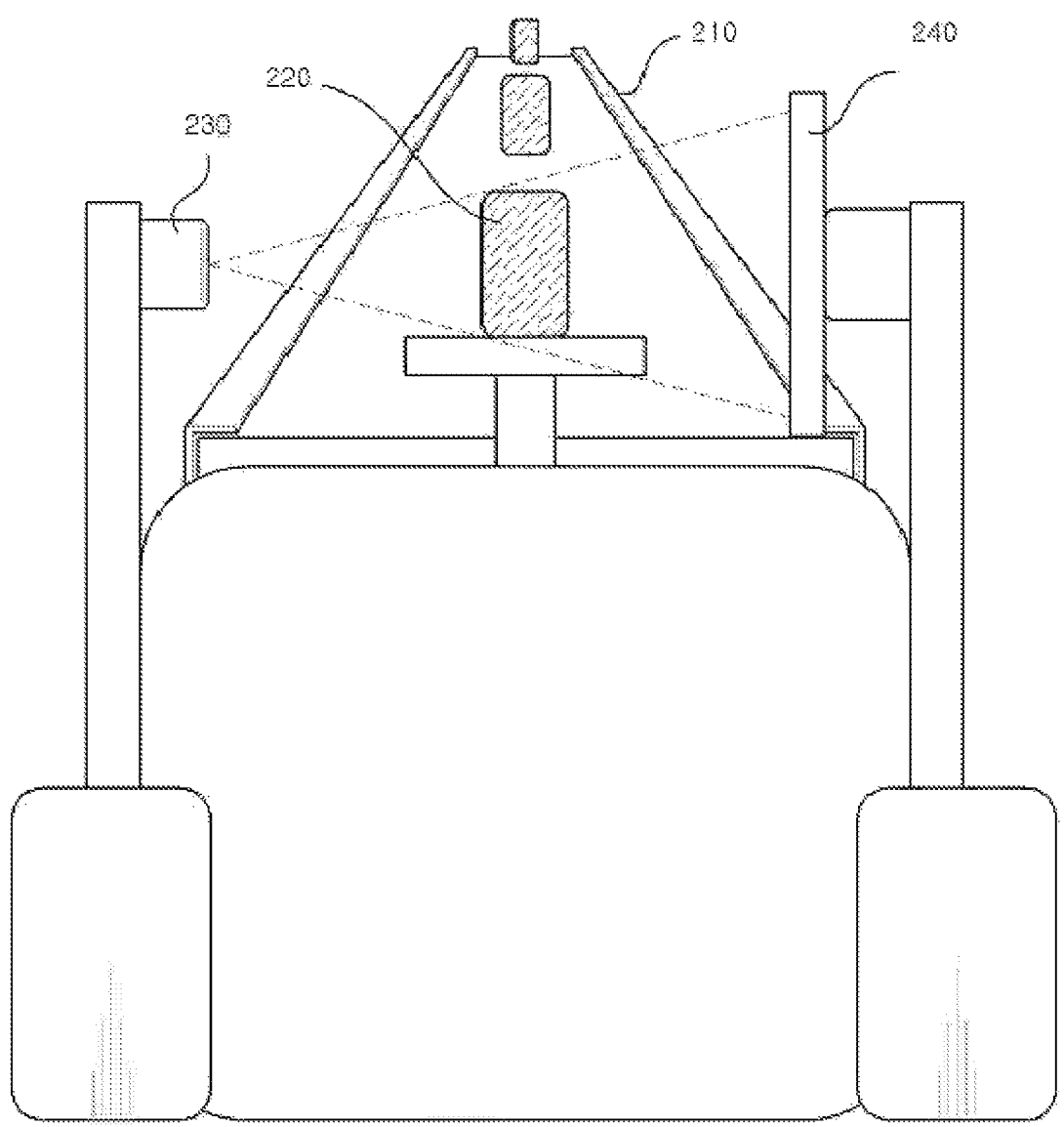
FIG. 2 is a diagram illustrating a state in which a subject is photographed using an X-ray inspection apparatus according to an exemplary embodiment of the present invention.
Figure 3:
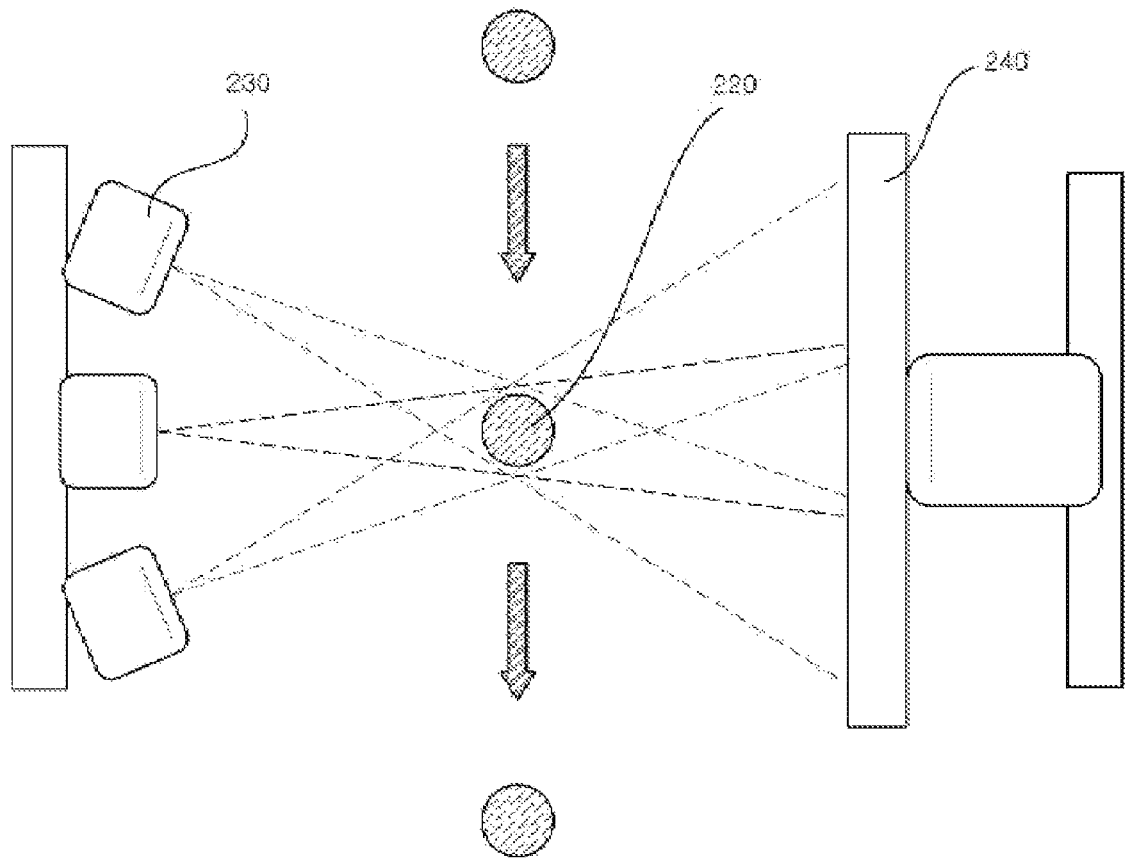
FIG. 3 is a plan view illustrating a subject photographing process according to the exemplary embodiment of FIG. 2.
Figure 4:
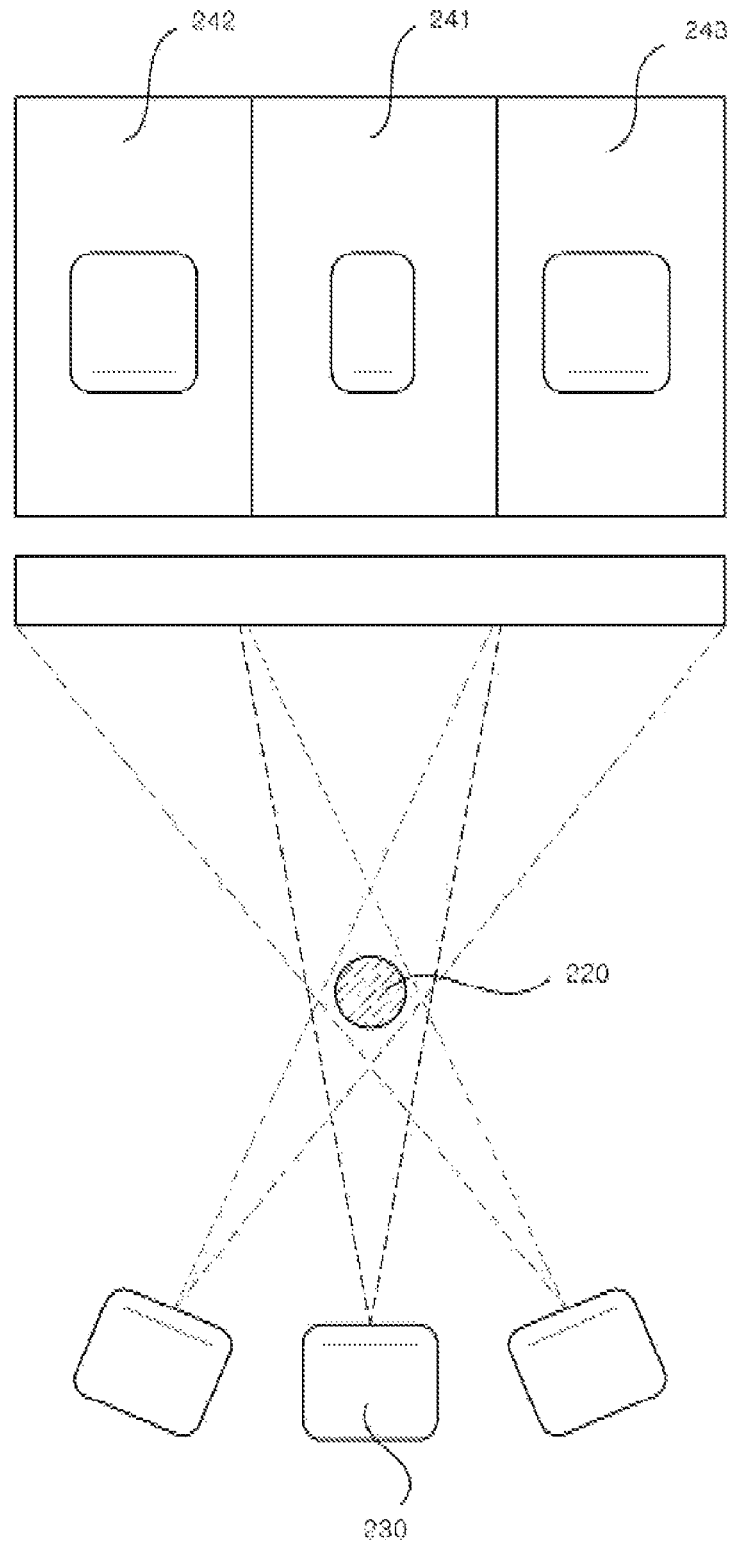
FIG. 4 is a diagram illustrating an X-ray inspection apparatus receiving three two-dimensional images through a detector according to the embodiment of FIG. 3.
Figure 5:
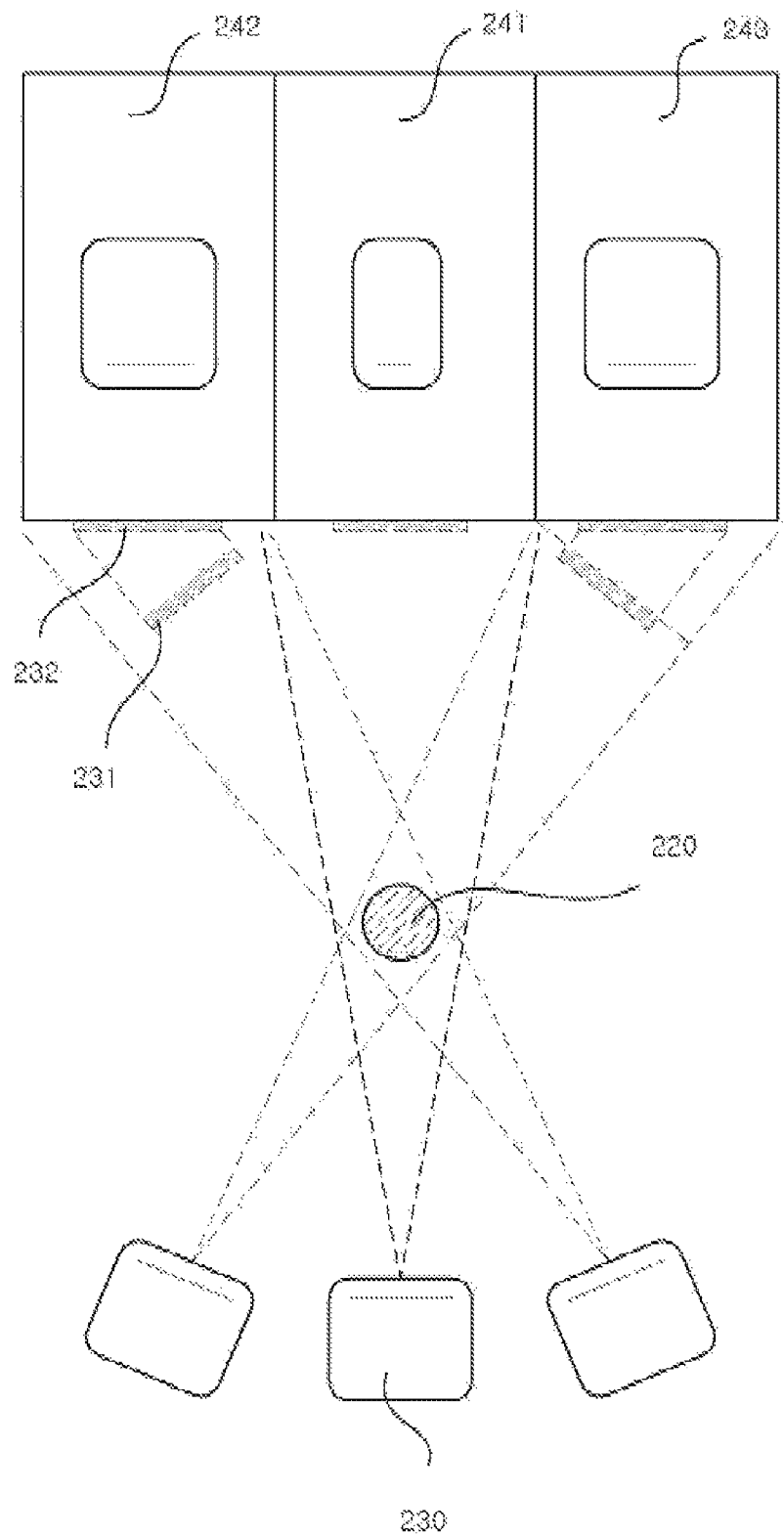
FIG. 5 is a diagram illustrating a process of generating distortion of an image received by a detector according to a photographing angle of a subject in the embodiment of FIG. 4.
Figure 6:
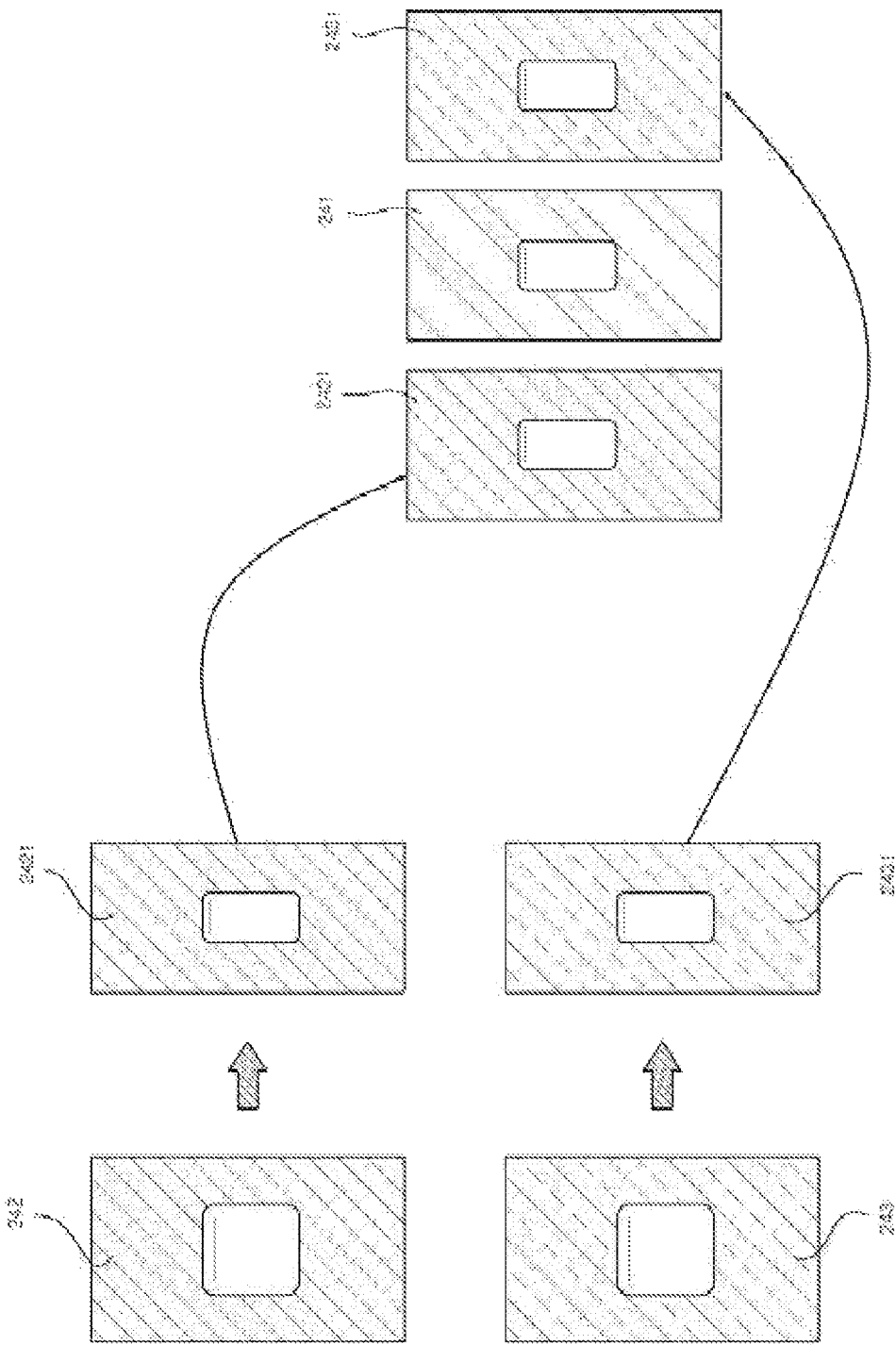
FIG. 6 is a diagram illustrating a process of correcting an image in which distortion occurs in the received image according to the embodiment of FIG. 5.
Figure 7:
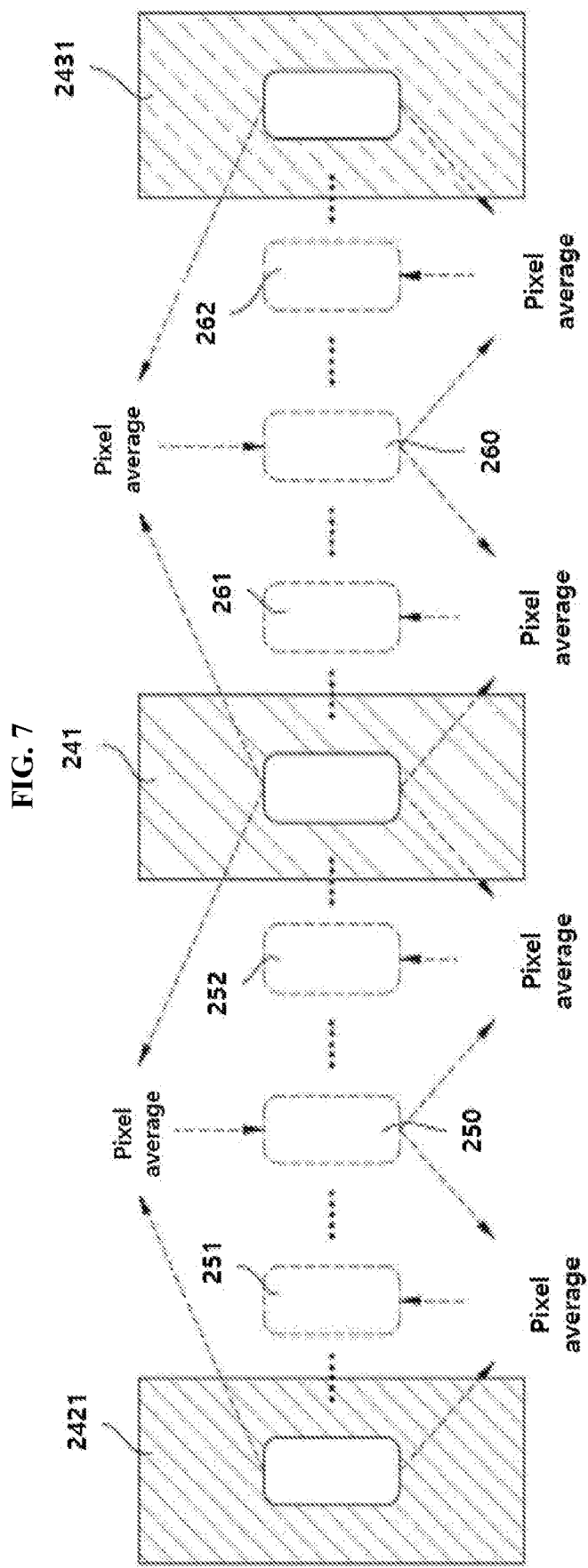
FIG. 7 is a diagram illustrating a process of generating a virtual image using a multi-dimensional 2D image received according to an embodiment of the present invention.
Figure 8:
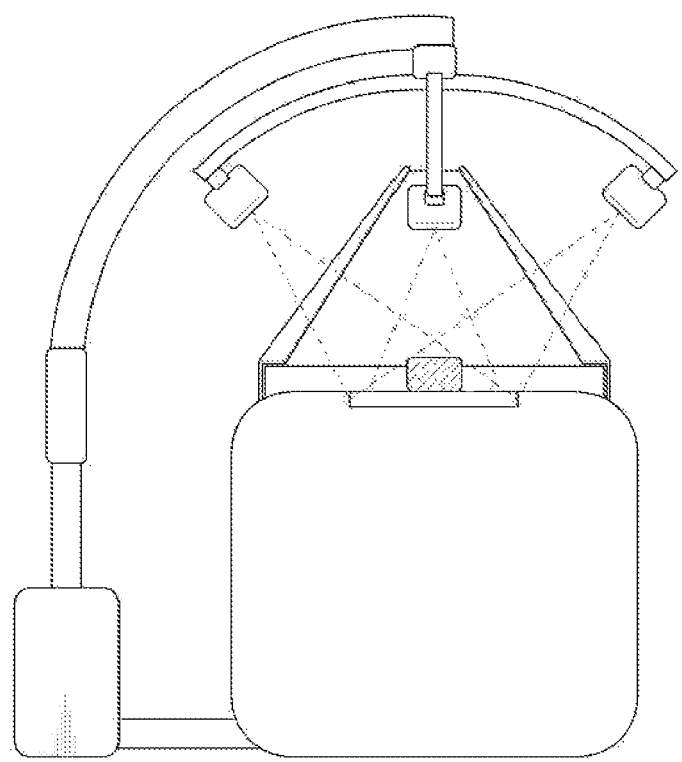
FIG. 8 is a diagram illustrating a subject photographing process using the X-ray inspection apparatus of various methods according to another embodiment of the present invention.

FIG. 1 is a flowchart illustrating a method for 3D image reconstruction according to an embodiment of the present invention. FIG. 2 is a diagram illustrating a state in which a subject is photographed using an X-ray inspection apparatus according to an exemplary embodiment of the present invention. FIG. 3 is a plan view illustrating a subject photographing process according to the exemplary embodiment of FIG. 2. FIG. 4 is a diagram illustrating an X-ray inspection apparatus receiving three two-dimensional images through a detector according to the embodiment of FIG. 3. FIG. 5 is a diagram illustrating a process of generating distortion of an image received by a detector according to a photographing angle of a subject in the embodiment of FIG. 4. FIG. 6 is a diagram illustrating a process of correcting an image in which distortion occurs in the received image according to the embodiment of FIG. 5. FIG. 7 is a diagram illustrating a process of generating a virtual image using a multi-dimensional 2D image received according to an embodiment of the present invention. FIG. 8 is a diagram illustrating a subject photographing process using the X-ray inspection apparatus of various methods according to another embodiment of the present invention.

First, referring to FIG. 1, in the step 110, an X-ray source may be radiated at a predetermined angle on a photographic subject, and a plurality of 2D image images received through a detector may be obtained.

As shown in FIGS. 2 and 3, the X-ray radiator 230 radiates an X-ray source from various angles to the subject 220 moving on the conveyor belt 210 to inspect a defect of a product (subject), and the 2D image may be obtained by receiving the X-ray at the detector 240.

Meanwhile, referring to FIGS. 4 and 5, in order to acquire a plurality of two-dimensional image images, a vertical image 241 generated by the X-ray source radiated in the vertical direction toward the detector 240 may be obtained. Also, the first side image 242 and the second side image 243 generated by the X-ray source radiated in a predetermined angle rotated direction in the first direction and the second direction based on the vertical image may be obtained.

In this case, in the case of the first side image 242 and the second side image 243, when the incident angle of the X-ray source emitted from the X-ray radiator 230 and the receiving angle of the detector are perpendicular (231), the distortion of the image will not occur. However, if the incident angle and the receiving angle are not perpendicular (232), image distortion occurs.

Therefore, in the case of the embodiment of the present invention, which emits the X-ray source toward the planar detector at various angles, because the incident angle and the receiving angle are not perpendicular to each other, the X-ray source radiating from the side may cause distortion of the image.

In the step 120, an image population may be generated by scaling the obtained plurality of 2D image images 241, 242, and 243.

In this case, in step 120, the first side image 242 and the second side image 243 may be scale-corrected to the size of the vertical image 241. Since the vertical image 241 is an area where the X-ray source is vertically incident, there is no distortion of the image, it is preferable to perform scaling correction based on this.

Referring to FIG. 6, for this purpose, the first side image 242 is scale-corrected to generate a first corrected image 2421, and the second side image 243 is scale-corrected to generate a second corrected image 2431. In this case, the generated first corrected image 2421 and the second corrected image 2431 may be aligned with the same scale as the vertical image 241.

In the step 130, a virtual image using a pixel average between two-dimensional images may be generated from the plurality of scale-corrected two-dimensional images and added to the image population.

More specifically, as shown in FIG. 7, the first virtual image 250 is generated between the vertical image 241 and the first corrected image 2421 using the pixel average between the vertical image 241 and the first corrected image 2421, and the generated first virtual image 250 may be added to the image population.

In a similar way, the second virtual image 260 is generated between the vertical image 241 and the second corrected image 2431 using the pixel average between the vertical image 241 and the second corrected image 2431, and the generated second virtual image 260 can also be added to the image population.

So, in this case, two virtual images 250 and 260 generated using pixel averages are added to three two-dimensional images 241, 242 and 243 generated through X-ray imaging, and thus five images 241, 242, 243, 250, and 260 may be stored in the image population.

Thereafter, in step 140, the virtual image generation is repeatedly performed by using a pixel average between two-dimensional images included in the image population until a number of two-dimensional images larger than a predetermined number P are generated in the image population.

That is, in the above example, by generating the first virtual image using the pixel average, the first virtual image and the second virtual image are generated, and five image images 241, 242, 243, 250, and 260 are sequentially stored in the image population. In addition, when the second virtual image generation operation is performed, virtual images may be generated between five image images, and thus four virtual images may be additionally generated.

In more detail, when the number of photographed 2D video images is M (ex. 3), the number of generated virtual images is $(M-1) \times 2^{n-1}$ each time the virtual image generating operation is performed n times, and thus by repeatedly performing the virtual image generation until the cumulative sum of the generated virtual images is larger than a predetermined number, it is possible to generate as many 2D images as necessary to reconstruct the 3D image.

In this way, since the total number of virtual images that can be generated by repeating n virtual image creation operations is $$(M-1)\sum_{k}^{n} 2^{k-1},$$

the generating of the virtual image may be performed until the total sum of the virtual images is equal to or greater than a predetermined number P. This may be expressed as follows by Equation 1 below.

$$P \le (M-1)\sum_{k}^{n} 2^{k-1} \quad \text{[Equation 1]}$$

where P is a predetermined number

Thereafter, in step 150, a 3D video image is generated using the generated 2D video image.

Therefore, by comparing the generated three-dimensional image with the good image it can be more accurately determine whether the product is defective.

Meanwhile, in one embodiment of the present invention, the X-ray inspection apparatus may be used in various forms. FIG. 8 is a diagram illustrating an x-ray inspection apparatus and a subject photographing process using the same according to another embodiment of the present invention.

Referring to FIG. 8, the X-ray inspection apparatus may be configured in a form in which a plurality of X-ray emitters is arranged at an angle of 90 degrees. In this case, the detector may receive four X-ray sources.

Accordingly, there are four two-dimensional images generated from four X-ray sources, and a virtual image using pixel averages may be generated from the four images. That is, three images are generated through the first virtual image generation, the virtual images generated through the second virtual image generation are 3×2=6, and the virtual image generated through the nth virtual image generation may be $$(M-1)\sum_{k}^{n} 2^{k-1}$$

as shown in Equation 1 above.

Therefore, even in this case, the virtual image generating operation may be repeated until the total sum of the generated virtual images is equal to or greater than the predetermined number P, thereby sufficiently generating the two-dimensional image for the three-dimensional image reconstruction.

As described above, according to an embodiment of the present invention, after acquiring a small number of 2D images, by generating a virtual image using the acquired image and using it to generate a 3D image, a 3D image reconstruction method capable of minimizing the exposure of radiation through at least 2D imaging may be provided.

In addition, according to an embodiment of the present invention, a three-dimensional image reconstruction method capable of realizing a three-dimensional image by minimizing image distortion may be provided by correcting the image scale between two-dimensional images taken from multiple angles and using them in three-dimensional image reconstruction.

In addition, the method for 3D image reconstruction according to an embodiment of the present invention may be recorded in a computer readable medium including program instructions for performing various computer-implemented operations. The computer readable medium may include program instructions, data files, data structures, and the like, alone or in combination. The program instructions on the medium may be those specially designed and constructed for the present invention, or they may be of the kind well-known and available to those having skill in the computer software arts. Examples of computer-readable recording media include hard disks, floppy disks, magnetic media such as magnetic tape, optical recording media such as CD-ROMs and DVDs, magneto-optical media such as floptical disks, and hardware devices specifically configured to store and execute program instructions such as ROM, RAM, flash memory, and the like. Examples of program instructions include not only machine code generated by the compiler, but also high-level language code that can be executed by a computer using an interpreter.

As described above, although one embodiment of the present invention has been described with reference to a limited embodiment and drawings, the present invention is not limited to the above-described embodiment. It is possible for those skilled in the art to various modifications and variations from this description. Accordingly, the present invention should be understood only by the claims set forth below, and all equivalent or equivalent modifications thereof will fall within the scope of the present invention.

What is claimed is:

1. A method for three-dimensional (3D) image reconstruction, the method comprising:

radiating an X-ray source at a predetermined angle to a photographic subject and obtaining a plurality of two-dimensional images received through a detector;

generating an image population by scale correcting the obtained plurality of two-dimensional images;

generating a virtual image from the plurality of scale-corrected two-dimensional images using a pixel average between the two-dimensional images and adding the virtual image to the image population;

repeating the generating of the virtual image using a pixel average between two-dimensional images included in the image population until a number of two-dimensional images are generated in the image population more than a predetermined number P; and generating a 3D video image using the generated two-dimensional images.

2. A method of claim 1, wherein the obtaining of the plurality of two-dimensional images comprises obtaining a vertical image produced by the x-ray source radiated vertically towards the detector, and a first side image and a second side image respectively generated by an X-ray source radiated in a predetermined angularly rotated direction in a first direction and a second direction based on the vertical image.

3. A method of claim 2, wherein the generating of the image population by the scale correction is characterized in that the first side image and the second side image are scale corrected to the size of the vertical image.

4. A method of claim 2, wherein the repetitively performing is characterized in that the virtual image is generated over a plurality of times, wherein 2n virtual images are generated at the time of nth generation, and the virtual image is repeatedly generated as many times as n corresponding to n calculated by Equation 1:

$$P \le \sum_{k=1}^{n} 2^k,$$

where P is a predetermined number [Equation 1].

* * * * *